US006893610B1

(12) United States Patent
Barnes

(10) Patent No.: US 6,893,610 B1
(45) Date of Patent: May 17, 2005

(54) AIR PURIFIER

(76) Inventor: Ronald L. Barnes, 74 Revere Way, Huntsville, AL (US) 35801

( * ) Notice: Subject to any disclaimer, the term of this patent is extended or adjusted under 35 U.S.C. 154(b) by 0 days.

(21) Appl. No.: 09/197,036

(22) Filed: Nov. 21, 1998

Related U.S. Application Data

(60) Provisional application No. 60/066,119, filed on Nov. 21, 1997.

(51) Int. Cl.[7] ................................................. A61L 9/20
(52) U.S. Cl. ............................. 422/4; 422/24; 422/121; 96/224
(58) Field of Search ............................. 422/4, 24, 121; 96/224

(56) References Cited

U.S. PATENT DOCUMENTS 4,990,311 A * 2/1991 Hirai et al. ............... 422/24 X
5,601,786 A * 2/1997 Monagan ................ 422/121 X
5,961,920 A * 10/1999 Soremark .................... 422/24

* cited by examiner

Primary Examiner—Elizabeth McKane
(74) Attorney, Agent, or Firm—Kenyon & Kenyon

(57) ABSTRACT

A system and method for purifying air is provided. An air purifier may include a housing, a means to move an airstream into the housing, and a pair of ultraviolet radiation generating means and associated control means to produce ozone to destruct airborne contaminants. The housing may be an elongated hollow tube, and the ultraviolet radiation generating means may be lamps of generally cylindrical shape axially aligned in the hollow tube. The control means may be lamp drivers and timers. The air purifier may further include a reactive filter across an exit means to reduce residual amounts of ozone in the stream of air passing through the exit means.

2 Claims, 4 Drawing Sheets

AIR PURIFIER

This application claims the benefit of provisional app. 60/066,119 filed on Nov. 21, 1997.

BACKGROUND OF THE INVENTION

This invention relates to a system, including both apparatus and a method, for purifying air by irradiating a stream of air selectively with ultraviolet light having a wavelength short enough to transform molecular oxygen ($O_2$) into ozone ($O_3$) or with ultraviolet light having a longer wavelength capable of destroying ozone so that it returns to stable molecular oxygen or with ultraviolet light having both wavelengths at the same time.

Ozone is an allotrope of oxygen that can be formed when molecular oxygen, such as the oxygen in the air, is irradiated by ultraviolet light having a relatively short wavelength between about 100 and 200 nanometers (nm.). This type of ultraviolet light, which is sometimes referred to as very-ultraviolet light, or VUV, is typically produced by evacuated ultraviolet generators, the radiant energy of which breaks stable molecular oxygen ($O_2$) into atomic oxygen (O), some of which then reforms as ozone ($O_3$).

Ozone can also be produced by subjecting air to an arc discharge of sufficient energy, but one of the disadvantages of doing so is that such an arc discharge can also ionize nitrogen, resulting in the production of compounds of nitrogen that are undesirable and even dangerous. VUV, on the other hand, does not ionize nitrogen in the air and, therefore, does not create those undesirable nitrous and nitric compounds.

Ozone is a powerful oxidizer because it is not a stable molecule. It has a half-life measured in hours, and immediately after being formed, ozone molecules begin to return to the stable, molecular state by releasing the third oxygen atoms which then enter into destructive reactions with contaminants in the vicinity. Some of the ozone breakdowns take place close to the VUV source, but other ozone molecules travel with any currents in the air as the ozone spreads out from the place it was formed. Additional reactions take place at locations increasingly remote from the origin.

The use of ozone in a room is desirable in terms of sterilizing or sanitizing or purifying the room. "Sterilizing" means to destroy all pathogens, i.e., anything that can grow biologically. "Sanitizing" means to reduce the level of pathogens down to some acceptable minimum level. "Purification" means to destroy pyrogens as well as pathogens. For example, ozone will break down alcohols and hydrocarbons as if they were being burned, i.e., converted to carbon dioxide.

One of the great advantages of ozone as a sterilizer is that it is not selective in the reactions it initiates. It renders harmful hydrocarbons and pyrogens (reactive molecules) harmless by oxidizing them, and it destroys pathogens (microorganisms), either by reducing or destroying them or by cell lysing or oxidation.

But the fact that ozone is not selective means that it will also react with humans and other mammals, and such reactions can be dangerous, even for short exposure if the levels of ozone are too high. They can also be dangerous if the exposure is too long, even if the levels of ozone are relatively low. Caution must be observed in the use of high concentrations of ozone in rooms and other closed spaces that are presently occupied by humans and other mammals or will be occupied before the concentration of ozone has been reduced to a sufficiently low level by breakdown of the ozone molecules. In the case of spaces to be occupied by humans, the Food and Drug Administration (FDA) has set certain time and concentration limits for exposure to ozone. The way the standards are set up is, it is appropriate to put the ozone into a room long enough at adequate concentration to sterilize the room and then to remove it.

In addition to destroying pathogens and pyrogens and oxidizing harmful hydrocarbons, another effect of ozone generally favorable to humans is that its release into a space typically causes insects to vacate that space.

Although the instability of ozone causes it to return to molecular oxygen, it takes a matter of hours for half of the ozone molecules to break down and if the concentration is high, it may take a long time for a room to become habitable by humans unless the process is speeded up. One method of doing so is by passing the ozone-containing air through reactive media, such as an activated carbon filter. This requires that the air be put into motion as an airstream through the filter. The ozone will be destroyed by reaction with the media, and the rate at which that takes place can be increased by raising the temperature of the reactive media.

Another method of destroying ozone in an airstream is to irradiate the airstream with ultraviolet light at a wavelength in the range between about 200 nm. and 450 nm., particularly 254 nm. Radiation in that part of the ultraviolet spectrum is referred to in the following description as UV. UV radiation increases the rate of disassociation of atoms in the ozone molecules and accelerates reaction of the ozone and its atomic oxygen components with airborne contaminants.

Ultraviolet light, itself, in any part of the ultraviolet spectrum has long been known to have a germicidal effect in clearing the environment of certain pathogens but is more limited than ozone in the types of air-borne contaminants it will attack. For example, ultraviolet light, alone, will sanitize and sterilize the air for bacteria, but not so much for certain pathogens, such as fungus and molds, nor will it attack pyrogens. Furthermore, ultraviolet light travels only in straight lines from its source and can only attack those pathogens that are along a line of sight from the source. As a result, even those pathogens that would be destroyed if they were irradiated by ultraviolet light will not be destroyed if they happen to be shielded by any opaque material, even a shield as small as a microscopic dust particle. Ozone, on the other hand, can circulate throughout a space into which it is propelled by an airstream and thus can react with contaminants in any part of that space. The use of UV is a very effective way of sanitizing air, but not totally sterilizing it.

OBJECTS AND SUMMARY OF THE INVENTION

It is an object of the invention to safely purify an enclosed space that contains pathogens, harmful hydrocarbons, and pyrogens by placing air in motion as an airstream and selectively irradiating the airstream with ultraviolet light at wavelengths that generate ozone from molecular oxygen in the airstream and, subsequently, at wavelengths that disassociate the ozone and return it to molecular oxygen before it has time to react in an undesirable way with people in a space reached by the airstream.

Another object is to provide means for moving a stream of air through a chamber that includes ultraviolet means to generate ozone and, downstream of such means, other ultraviolet means to destroy the ozone, the ozone generation means and the ozone destruction means being operated selectively to achieve, at certain times, a net increase in the amount of ozone in the environment in which the chamber is located and, at other times, a net decrease in the amount of ozone in that environment and, at still other times, no generation of ozone at all while still irradiating the airstream with ultraviolet light for its germicidal effect.

A further object is to activate the ozone-generating means and the ozone-destroying means selectively to control the concentration of the ozone in an environment.

Still another object is to provide a chamber through which a stream of air passes and which includes controllable ultraviolet ozone-generating means, means to measure the concentration of ozone in the stream, and controllable ultraviolet ozone-destruction means to provide a desired degree of purification of the stream of air.

Yet another object is to include, within a chamber housing ultraviolet ozone-generating means, means to reflect ultraviolet light so that it can strike pathogens that would otherwise not be in a direct line of sight from the ultraviolet ozone-generating means.

Another object is to control the length of time, from zero to a predetermined maximum, in which a stream of air is exposed to ozone-producing VUV radiation and, subsequently, to UV radiation.

A further object is to provide means to control the concentration of ozone by controlling the relative operation of means capable of producing ultraviolet radiation in a wavelength band capable of transforming molecular oxygen into ozone and of means capable of producing ultraviolet radiation in a wavelength band that causes the disassociation of ozone molecules.

To those skilled in this technology, additional objects may become apparent after studying this disclosure.

In accordance with this invention, a closed space can be purified to a controlled extent by creating a moving stream of air in that space and irradiating a concentrated part of the airstream for a selected length of time with VUV radiation that has an appropriate intensity in a wavelength in the range of about 100 to 200 nm. to transform oxygen in the airstream into ozone. Directing the stream of air to flow close to the VUV source enhances the efficiency of this transformation. Impelled as part of the airstream, the ozone is allowed to circulate throughout the space to react with contaminants in all parts of the space.

If the ozone-containing airstream is to be directed on into a space occupied by people at that time or later, the concentration of the ozone at the time of such occupation must be limited to a permissible level. If no one is in the space at the time the ozone is introduced, all that need be done is simply to turn off the source of VUV radiation and allow enough time to pass before allowing people back in. However, if, as is frequently the case, the concentration of ozone in the space must be reduced more quickly in order to permit people to reenter the space with less delay, a stream of the ozone-laden air can be extracted from the space and directed through UV radiation.

The shorter wavelength ultraviolet radiation required to produce ozone may be generated by system that includes: means to create a moving stream of air through a housing; and one or more VUV generating means within the housing to irradiate the airstream. After being moved past the VUV generating means, the air is moved out of the housing by way of an opening that allows the airstream to exit to the surrounding space. If nothing is done to decrease the ozone in this airstream, the concentration of ozone in the surrounding space will eventually reach a maximum value that depends on such things as the generating capacity of the VUV generating means, the volume of air to be affected, and the contaminant load in that volume.

Between the VUV generating means and the output opening, the ozone-containing airstream is moved past at least one UV generating means, which, if activated, disassociates ozone in the stream to return the ozone its stable, molecular $O_2$ state.

The system also comprises ozone measuring means to measure the concentration of the ozone in the airstream and to control the operation of both the VUV means and the UV means to be sure that there will not be an excess of ozone when the space reached by the airstream is occupied by people.

There are three basic modes of operation of the VUV means and the UV means. The first is a light-duty mode in which only the UV means are actuated to use the germicidal effect of UV, alone, for general cleaning and sterilization of the air. In the second mode, which is useful in eliminating the most difficult odors and in destroying deleterious contaminants, the airstream is exposed to VUV radiation but not to UV radiation. The second mode should only be used when no humans or other mammals are in the environment reached by the airstream, or are in that environment for only a very limited time. Operation in this mode is limited by timing means that can be set to allow the VUV means to operate for any length of time, typically up to about 3.5 hrs. if no humans are present, but only for far shorter periods of time if humans or other mammals must be in the environment while the device is working. In the third mode, which is useful for controlling odors and for air sterilization, the VUV means generate ozone which is then exposed to UV to destroy most of the remaining ozone after the originally generated ozone has had time to react with at least some of the undesired matter in the airstream.

DESCRIPTION OF A PREFERRED EMBODIMENT

Figure 1:
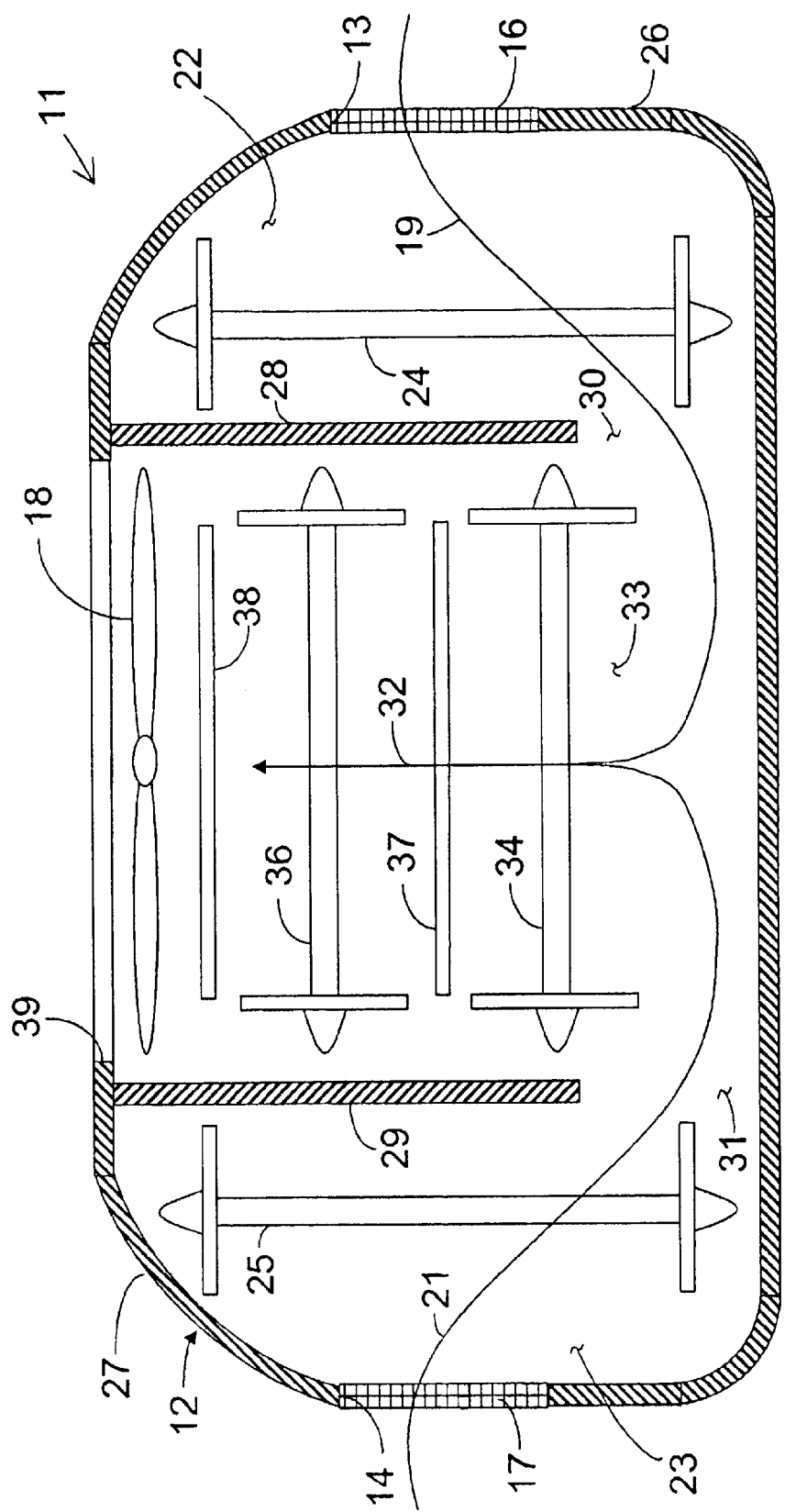
FIG. 1 is a cross-sectional view of an air purification device for moving a stream of air past VUV means for controllably generating ozone and UV means for destroying the ozone.

The unit 11 shown in FIG. 1 is a preferred embodiment of the invention at the present time. In this embodiment, the unit 11 constitutes a sanitizer/sterilizer and includes a housing 12 that has entrances 13 and 14 covered by filters 16 and 17, respectively, to catch at least some of the air-borne particles that would otherwise enter the housing 12. A fan 18 draws air into the housing through the filters and creates airstreams 19 and 21 indicated by arrows. After passing through the entrances and the filters, the air in the streams enters regions, or chambers, 22 and 23 in which sources 24 and 25 of VUV radiation are located. The exterior walls 27 and 28 of the chambers 22 and 23 as well as the interior walls 28 and 29 and the filters 16 and 17 of those chambers are opaque to ultraviolet radiation so that none will escape into any other part of the unit 11 or out to the surrounding space. In this embodiment only one of the VUV sources is shown athwart each of the entrance chambers, although the unit 11 may have multiple VUV sources in each entrance chamber if more intense radiation is desired. The radiation emitted by each of the VUV sources 24 and 25 is in the shorter wavelength part of the ultraviolet spectrum, between about 100 nm. and 200 nm. and, especially, about 185 nm.

While the arrows make it appear that the airstreams 19 and 21 flow smoothly through the chambers 22 and 23, this is not actually the case. It is desirable that the air circulate somewhat turbulently in the chambers to get sufficient exposure to the VUV radiation. It is well known that VUV radiation transforms molecular oxygen into ozone by disassociating some of the molecules of $O_2$ into separate atoms of O, some of which then combine with other molecules of $O_2$ as molecules of ozone ($O_3$). However, before combining into molecules of ozone, some of the atomic oxygen may react destructively with some of the contaminants in the entrance chambers 22 and 23. The VUV radiation also destroys some contaminants in those chambers. Furthermore, some of the ozone molecules immediately start to react with other contaminants in the airstreams passing through the entrance chambers 22 and 23.

Air does not linger in the entrance chambers; in a relatively short time, air in the streams 19 and 21 follows the arrows through openings 30 and 31 to converge into a single airstream 32 in a central region, or chamber, 33 in which the movement of the air is also turbulent. The central chamber in this embodiment contains two UV sources 34 and 36 that emit radiation in the UV portion of the ultraviolet spectrum, between about 200 nm. and 450 nm. and, particularly, at about 254 nm. It is well known that radiation in this part of the ultraviolet spectrum destroys ozone remaining in the airstream 32, ultimately causing it to return to stable molecular oxygen unless it has reacted with matter in the airstream.

Atomic oxygen created in the central chamber 33 from disassociation of the ozone immediately begins to react with and destroy pyrogens and pathogens there. In addition, the remaining microorganisms that are in a line of sight from the UV sources will be affected by the germicidal effect of ultraviolet radiation from the UV sources 34 and 36. Reflectors 37 and 38 are placed between the UV sources and an exit 39 to increase the exposure of the airstream to UV radiation in order to further reduce or eliminate residual ozone and react with contaminants. Reflection of the UV radiation makes it possible to strike and destroy those pathogens within its destructive capacity and which would otherwise be hidden from UV radiated directly from the UV sources 34 and 36. The reflectors also shield UV radiation from the sources 34 and 36 from escaping through the exit 39.

Figure 2:
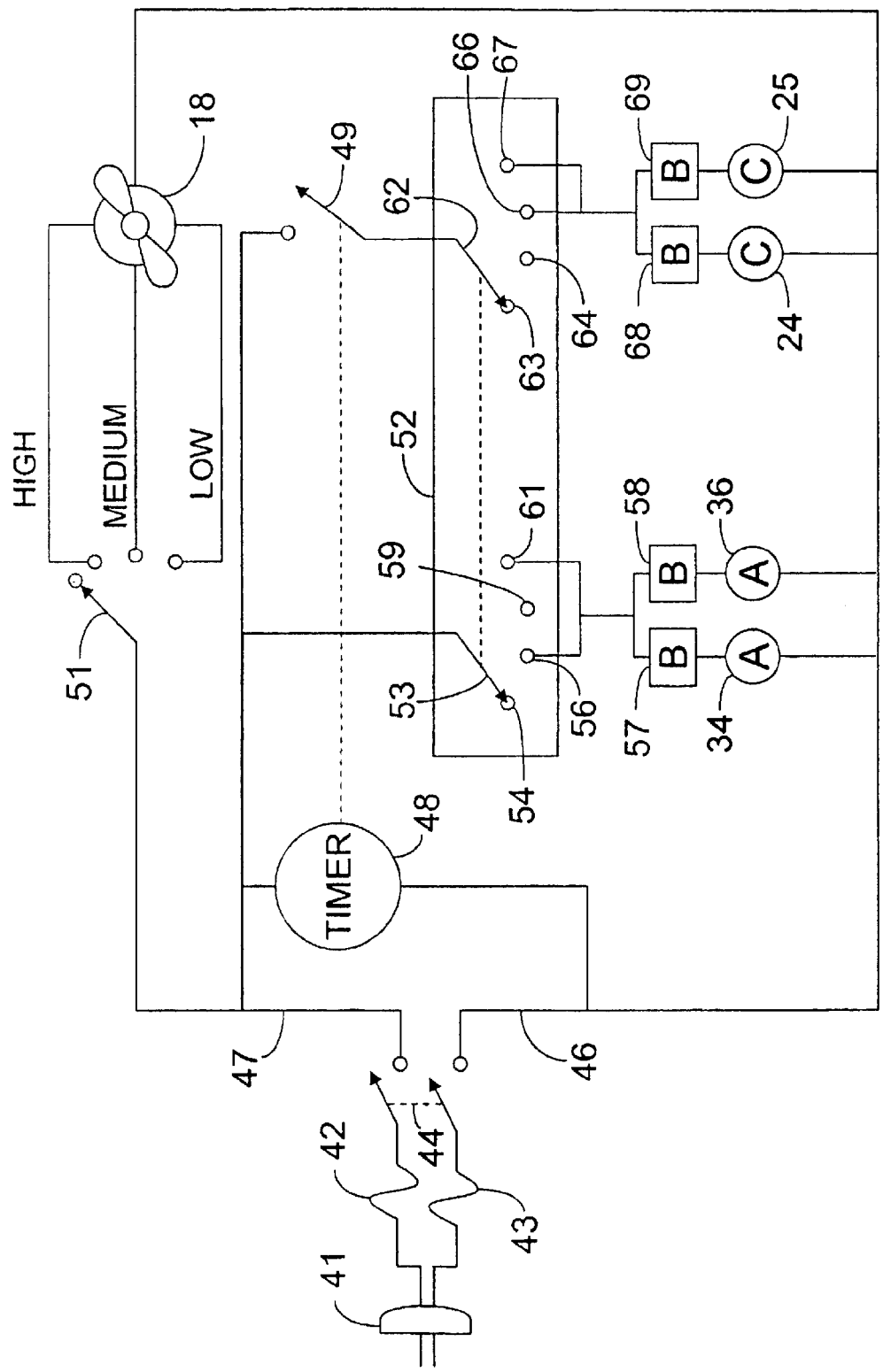
FIG. 2 is a schematic diagram of a circuit for operating the device in FIG. 1.

FIG. 2 is a schematic diagram of the circuit in the unit 11. This embodiment is set up to operate from standard 110 v. a.c., and it includes a plug 41 to be plugged into a standard outlet. Fuses 42 and 43 are connected in series with each power line along with one of the poles of a two-pole-single-throw switch 44. One of the lines 46 to the right of the switch may be considered the common wire and the other the hot wire 47. A timer 48 connected directly to the lines 46 and 47 can be actuated when the circuit is turned on, and a switch 49 is connected electrically to the line 47 and mechanically to the timer to be opened after a length of time determined by a setting programmed into the timer 48 by a user of the unit 11.

A manually controlled four-position switch 51 connects the line 47 to the fan 18, or, more specifically, to the fan motor. The arm of the switch is shown engaging the first contact, to which nothing is connected. With its arm in this position, the switch 51 is in the "off" position in which the fan motor does not receive operating power. The other three contacts of the switch are marked, successively, HIGH, MEDIUM, and LOW and are connected to terminals on the fan motor to control its speed to be high, medium or low according to the number of cubic feet per minute of air considered to be necessary. In general, the larger the space to be treated, the higher the speed of the fan. The fan motor 18 has another terminal connected to the common line 46 to complete the power circuit for the fan motor.

The unit 11 also includes a two-layer-four-pole switch 52 to control the VUV sources 24 and 25 and the UV sources 34 and 36. The first layer of the switch has an arm 53 connected directly to the line 47 and shown in its first, or "off," position engaging an open contact 54. The second contact 56 that the arm 53 can engage is connected to one end of a parallel circuit comprising the two UV sources 34 and 36, each of which has a ballast 57 and 58, respectively, connected in series with it. The other end of that parallel circuit is connected to the common line 46. The third contact 59 that the arm 53 can engage is another open-circuit position, and the fourth contact 61 is connected directly to the second contact 56 and, therefore, to one end of the parallel circuit comprising the UV sources 34 and 36 and their ballasts 57 and 58.

The switch 49 is connected in series between the line 47 and the arm 62 of the second layer of the switch 52. This arm, which is ganged with the arm 53, can also be set to engage any one of four contacts: an open contact 63 in the first, or "off" position; a second contact 64 to which nothing is connected; a third contact 66; or a fourth contact 67. The third and fourth contacts are short-circuited together and connected to one end of another parallel circuit comprising the VUV source 24 and a ballast 68 in one leg and the VUV source 25 and a ballast 69 in the other leg. The other end of this parallel circuit is connected to the common line 46.

The unit 11 can be operated in several modes of operation determined by the setting of the switch 52. In each mode, the switch 51 has to be changed from the "off" position in which it is shown to one of the other positions in order to set a stream of air in motion through the unit 11. The speed selected for the fan depends on the amount of air that must be moved and the velocity at which it is to be moved.

In the first mode, the switch 52 is set to its second position, in which the arm 53 engages the contact 56 and the arm 62 engages the open contact 64. In this position, current can pass through the arm 53 to turn on the UV sources 34 and 36. At the same time, no current will flow through the arm 62 and the open contact 64, even if the switch 49 controlled by the timer 48 is closed. This mode provides sterilization by ultraviolet irradiation of air passing through the unit in a manner long known. If there is any ozone in the air being brought into the unit 11 by the fan in this mode, it will be destroyed by irradiation by the UV inside the unit.

In the second mode, the arms 53 and 62 are set to their third positions to engage the contacts 59 and 66, respectively. The contact 59 is not connected to anything, so no current will flow through the arm 53, but the contact 66 is connected to the parallel circuit comprising the VUV sources 24 and 25. If the switch 49 is set in its closed position by the timer 48, current can flow through the contact 66 and the VUV sources, causing them to generate ozone from molecular oxygen drawn into the entrance chambers 22 and 23. The timer is convenient for controlling the operation of the VUV sources 24 and 25 so that they will generate ozone only when it is safe to do so, i.e., when people are not in, or are only briefly in, the space to be treated. If no one is to be in the space for several hours, such as all night, the timer 48 can be set to allow the VUV sources to be operated for most of that time and to be turned off long enough at the end of that time to allow all of the ozone to disintegrate. However, if it is necessary to generate ozone will people are in the room, the timer may be set to allow the switch to be closed and ozone to be generated for repeated short intervals of time, such as a few minutes each hour.

As the ozone from the VUV sources 24 and 25 pervades the room, it is capable of destroying odors, pyrogens, and pathogens including not only bacteria and viruses but also funguses, molds, and alcohol that might be in the air. In addition, the ozone renders reactive metal particles in the air inert by oxidizing them so that they become incapable of reacting with other materials. In effect, the oxidation of these contaminants by the ozonator unit 11 burns them so that they are no longer toxic.

Figure 3:
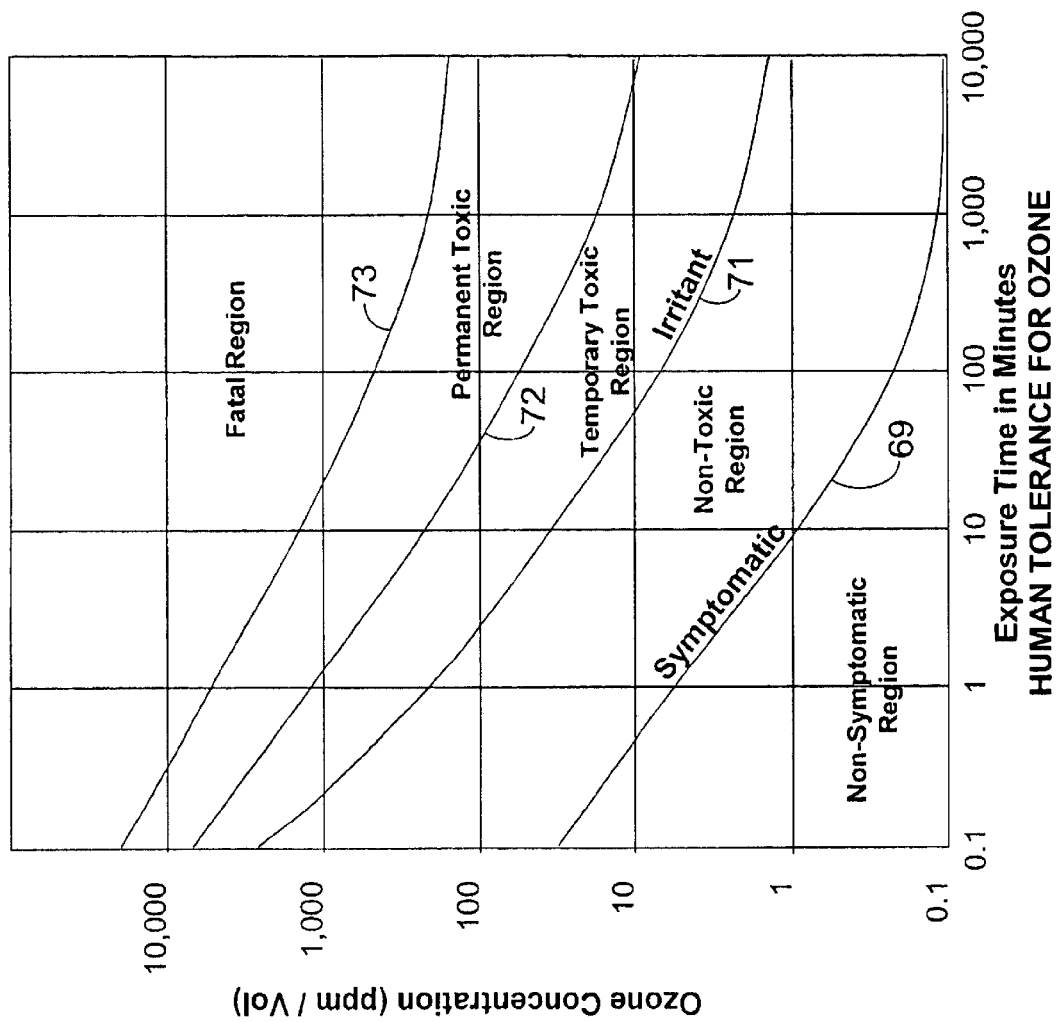
FIG. 3 is a set of curves representing human tolerance for ozone.

The reason for limiting the time people can be exposed to ozone generated in the unit 11 is that ozone can be an irritant to people in the room. While it is not considered to be toxic, there are indications that exposure to ozone at a high enough concentration for a long enough period can actually cause pneumonia because of irritation of the lungs. FIG. 3 is a graph obtained from OSHA indicating the approximate effect on humans of exposure to ozone at various levels. If the concentration of ozone and the time of exposure are below the lowest curve 69 marked "Symptomatic", there should be no adverse effect on humans. Exposure to ozone in concentrations and for times above that curve and below the next curve 71 marked "Irritant" are considered to be non-toxic. Humans should be able to tolerate exposure to ozone in concentrations and for lengths of time in the region above the curve 71 and below the curve 72 long enough to perform temporary, or short, tasks, but above the next curve 73, the ozone concentration in the region marked "Fatal Region" is so high that no exposure should be permitted. However, the information in FIG. 3 is not considered to be absolutely reliable. As a result, the FDA requires that exposure to ozone be limited to 1 ppm for eight hours, which is the region below the bottom line on the graph.

Parenthetically, it may be noted that some areas of the country have intense smog with an ambient ozone level of 1 ppm., just from natural causes. In those places, it may be helpful to use the unit 11 in the first mode in a closed building to remove the ozone created by the natural causes.

In the third mode, the switch 49 is closed and the arms 53 and 62 are set in their third positions in which they engage the contacts 61 and 67, respectfully. This energizes the UV sources 34 and 36 as well as the VUV sources 24 and 25. VUV radiation from the sources 24 and 25 generate ozone from molecular oxygen in the air drawn into the entrance chambers 22 and 23, and this ozone immediately begins to sterilize and purify that air. At the same time, there is some sterilization of that air directly by exposure to the VUV radiation. As the air containing ozone is drawn into the central chamber 33 by the fan 18, the ozone remaining in that air continues to attack contaminants, and this effect ia enhanced in the central chamber by operation of the UV generators 34 and 36. which cause the third oxygen atoms of ozone molecules to separate and to be in the highly reactive state that enhances their ability to react with contaminants that have not been reacted with up to that time. Thus, although the UV radiation from the sources 34 and 36 would seem to have an undesired effect by initiating the return from ozone to molecular oxygen, this return causes the extra oxygen atoms to pass through a state in which they are even more reactive with contaminants than they would be if they continued to be parts of ozone molecules up to the time they encountered contaminant particles.

The sanitization of an unoccupied room by operation of the unit 11 in the third mode can be further controlled by operation of the fan switch 51 and the timer 48 to cause the unoccupied room to be sanitized by high levels of ozone initially and then returned either the condition in which there are still acceptably low levels of ozone or to the condition in which there is complete elimination of the ozone.

Some of the contaminants that ozone can react with are toxic if they are inhaled, and reaction with such sources of irritation is one of the important benefits of the unit 11. For one thing, ozone breaks up or modifies long chains of very complex molecules, such as odor from tobacco smoke, which is a long, organic chain. Ozone will disrupt that chain, thereby eliminating its odor. Tobacco smoke is a gummy tar with a nicotine virus built into it and is, therefore, particularly undesirable in the ventilating system of a car. All these things, which can be irritants if breathed heavily for awhile, are destroyed by ozone.

The ability of ozone to break down long, organic chains can also be very useful in eliminating other odors that accumulate in the heating and air conditioning system of an automobile. Cars sometimes get very hot and at other times very cold, and since they are outdoors much of the time, they pick up a lot of contaminants. Since, the air circulating system in the car typically has no filter in it, these contaminants get all over wall surfaces in the system and need to be eliminated. Even if it is not desirable to destroy all the contaminants on the wall of the ventilating system continually, it may be very desirable to have the capacity to do so at specific times. Putting the unit 11 in an automobile, setting the unit to generate ozone, and turning on all the air conditioning and circulating equipment, causes the ozone to go through all the little radiators in the ventilating system and destroy, the smoke molecules, the nicotine viruses, and other contaminants adhering to the walls of the ventilating system.

Another advantage of ozone is that it reacts with molecules in the halogen group by replacing the halogen with oxygen, which essentially changes a molecule that would be toxic into one that is non-toxic. So, almost across the board, ozone converts toxic pyrogens to non-toxic waste.

Figure 4:
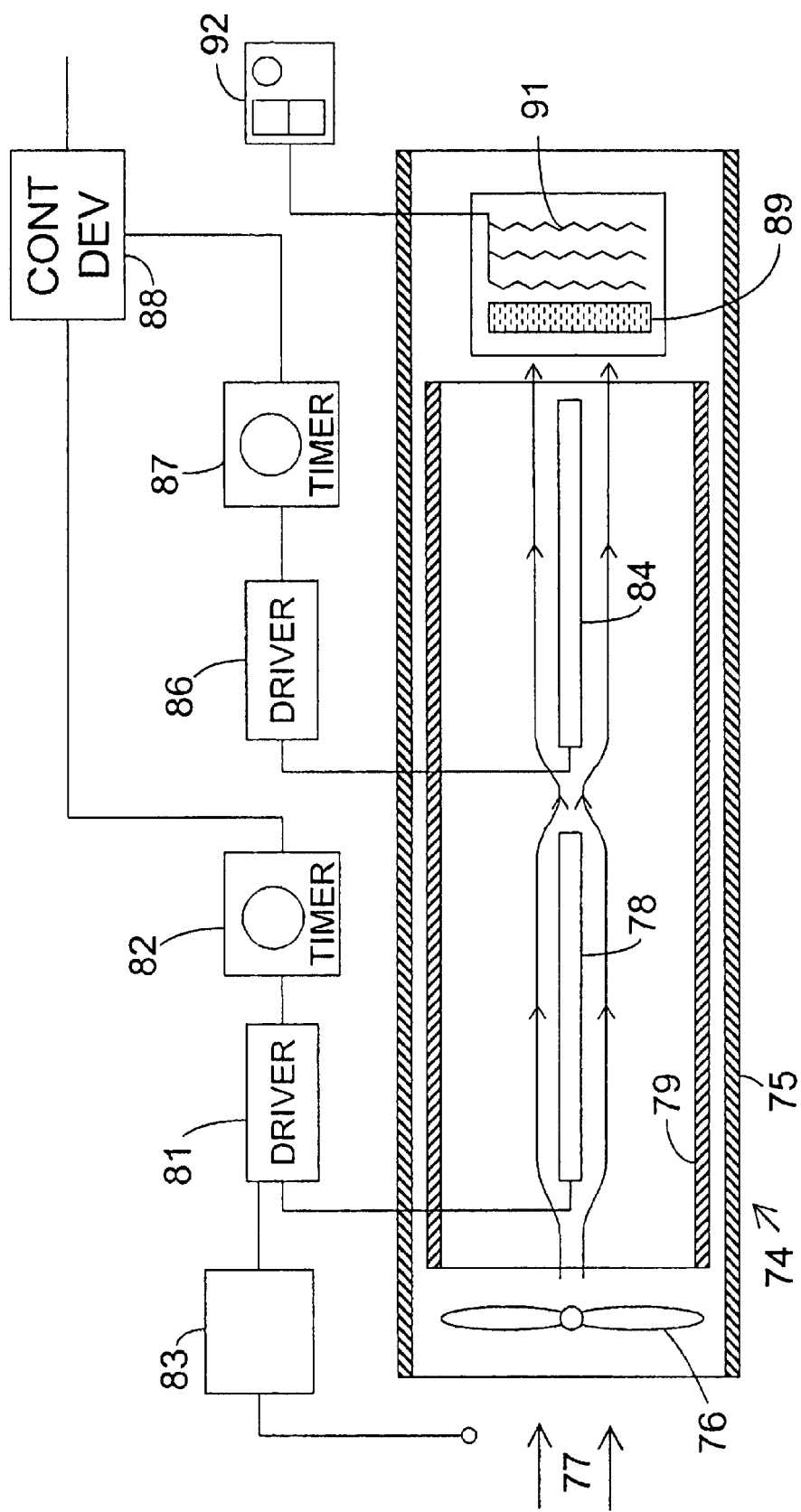
FIG. 4 is a cross-sectional view of an alternative device for controllably generating and destroying ozone in a stream of moving air.

FIG. 4 is a schematic representation of a unit 74 that constitutes a second embodiment of this invention. The basic structure of this unit is a duct 75 open at both ends. A fan 76, shown in this embodiment as being located at the input end of the duct, produces an airstream 77 that flows into that end of the duct and on though a space of annular cross section between an elongated lamp 78 and a tubular reflector 79. The lamp is a source of VUV radiation, and the reflector is formed either on the inner surface of the duct 75 or as a separate tubular member within the duct. Electric current to energize the VUV source 78 to produce ozone is derived through a lamp driver 81 controlled by a timer 82. As previously described in connection with the embodiment in FIG. 1, the timer can be set to operate the VUV source continuously for a selected period of time or intermittently according to the amount of ozone required to react with contaminants to sanitize the airstream 77 and the room within which the unit 74 is located. Pathogens that can be destroyed by ultraviolet radiation passing through the airstream are further attacked by the VUV, directly. The lamp driver is also connected to an ozone sensor 83 that includes both an ozone-sensitive component and a control unit, making it capable of measuring ozone in the air reentering the unit 74 after having circulated through the room in which the unit is located. The sensor is connected to the lamp driver 81 to control the operation of the lamp driver to cause the VUV source 78 to continue to produce ozone until the desired concentration in the room, as measured by the sensor 83 in the air that finds its way back to the input end of the unit 74, is obtained.

The unit 74 also includes a second lamp 84 that constitutes a source of UV downstream of the VUV source 78. The UV source derives its operating current from a second lamp driver 86 controlled by a second timer 87. Both of the timers 82 and 87 are connected to an ozone-measuring and control device 88. The UV source 84 disassociates the ozone in the airstream 77 flowing past it, thereby accelerating the reaction of the resulting atomic oxygen with pathogens and pyrogens in the airstream, and further sterilizing and sanitizing the air in the unit 74. In so doing, the UV from the source 84 speeds up the return of the room in which the unit 74 is located to an ozone-free condition. This reduces the time humans would have to remain out of the room if the ozone molecules only disassociated at the normal rate. UV radiation from the source 84 also assists in destroying pathogens, both by direct impingement on those pathogens and by reflected impingement on them from the reflector 79.

An organic or highly reactive filter 89 is included in the exit end of the unit 74 to trap contaminants and to assist in destroying residual ozone molecules remaining in the airstream 77 as it leaves the unit. This has two effects: it sterilizes the filter 89 by reaction of the ozone and atomic oxygen with the trapped contaminants, thereby making the filter more reactive with respect to contaminants arriving later, and it assists in destroying more of the residual ozone in the airstream 77. The filter 89 is not needed under all modes of operation of the unit 74 and may, therefore, be removable. A heater 91 associated with the heater can be used to increase the rate of destruction of ozone by raising the temperature of the filter.

The amount of sterilization and sanitation within the exit airstream 77 as it exits from the duct 75 and the amount of residual ozone in it can be controlled in several ways. One way is to adjust the speed of the fan 76 to change the speed of the airstream 77. Another way is to use the ozone sensor 83 make the lamp driver 81 inoperative when the concentration of ozone in air returning to the unit 74 gets up to a selected level. Yet another way is to use the control device 88 to control the operation of the VUV source 78 and the UV source 84. The control device can control the timer 82 to determine the timing of intervals when the VUV source is energized to generate ozone, and can control the timer 87 to determine when the UV source 84 is energized to destroy the ozone. The sterilization and sanitation of the airstream 77 can also be controlled by means of a heater control 92 to which the heater 91 is connected and which sets the intensity of heat and the times the heater is turned on.

Using these controls, the unit 74 can operate is several different modes. In one, it can provide a high level of ozone in the airstream 77 to sanitize the air in a room by fully energizing the fan 76 and the VUV source, with the filter 91 removed from the airstream. The VUV source is controlled by the timer 82 so that the system can operate in this mode only during intervals when people are not in, or are only briefly in, the room being sanitized. As a further safety measure, the timer 82 can be set to allow operation of the VUV source 78 for only brief intervals, for example, 15 minutes at a time.

A second operating mode is to provide sterilization of the airstream 77 in the unit 74 and to remove residual ozone from the airstream without generating any further ozone in the airstream. In this mode, only the fan 76 and the UV source 84 are turned on. The filter 89 may be in place.

A third mode of operation provides maximum sterilization and sanitation within the unit 74 and low levels of ozone output. In this mode, the filter 89 is in place, and the fan 76, the VUV source 78, the UV source 84, and the heater 91 are operated at maximum output. If the level of ozone is to be automatically controlled to be low, the ozone level sensor 83 and control 84 can be used to cycle the intensity of the VUV source 78 and the filter heater 91.

A fourth mode of operation can be used to allow an unoccupied room to be sanitized by a high level of ozone initially by having both VUV and UV sources 78 and 84 turned on and the speed of the fan 76 and the heater 91 operated at their highest respective settings. This condition is cycled by the timer 82 and 87 to return to either of the modes having low levels of ozone, or to the mode causing complete elimination of the ozone. Maximum sterilization is provided with ozone levels controlled by the ozone level sensor 83.

While this invention has been described in specific terms, it will be recognized by those skilled in this technology that modifications may be made therein within the scope of this invention.

What is claimed is:

1. An air purifier system comprising:
   (a) a housing comprising:
      (i) entrance chamber means to receive air from outside the housing, and
      (ii) second chamber means communicating with the entrance chamber means to receive air therefrom and comprising exit means through which to expel air from the housing;
   (b) means to move an airstream into the housing through the entrance chamber means and on through the second chamber means and out through the exit means;
   (c) first ultraviolet radiation generating means in the entrance chamber means to produce very ultraviolet radiation having a wavelength less than about 200 nm.;
   (d) first control means to control the first ultraviolet radiation generating means to irradiate the airstream in the entrance chamber means for first selected intervals of time to react destructively with airborne contaminants in the entrance chamber means and to react with molecular oxygen in the airstream in the entrance chamber means to produce ozone to react destructively with contaminants in the housing and beyond the housing;
   (e) second ultraviolet radiation generating means in the second chamber means downstream of the first ultraviolet radiation generating means to generate radiation having a wavelength greater than 200 nm.;
   (f) second control means to selectively energize the second ultraviolet radiation generating means for second selected intervals of time to irradiate the airstream in the second chamber means with ultraviolet radiation having a wavelength greater than 200 nm. to react destructively with airborne contaminants in the second chamber means and to react destructively with ozone in the airstream in the second chamber means;
   (g) wherein the housing comprises an elongated hollow tube, a first end portion of which comprises the entrance chamber means and the opposite end portion of which comprises the second chamber means, with the exit means at the remote end of the tube from the first end portion;

(h) wherein the first and second ultraviolet radiation generating means are lamps of generally cylindrical shape axially aligned in the hollow tube;

(i) wherein the first control means to control the first ultraviolet radiation generating means comprises a first lamp driver and a first timer to control the operation of the first lamp driver;

(j) wherein the second control means to control the second ultraviolet radiation generating means comprises a second lamp driver and a second timer to control the operation of the second lamp driver; and;

(k) wherein the air purifier system further comprises a reactive filter across the exit means to reduce residual amounts of ozone in the stream of air passing through the exit means.

2. A method of controlling ozone in air in a selected space, said method comprising the steps of:

(a) creating a moving stream of the air from the selected space into a sub-space in the selected space to draw the air in the selected space through the sub-space and back into the selected space;

(b) selectively irradiating the air in an upstream part of the sub-space with very ultraviolet radiation having a wavelength less than about 200 nm. and an intensity sufficient to generate ozone molecules in the steam of air moving through the sub-space;

(c) irradiating air in a downstream part of the sub-space for a selected interval of time with ultraviolet radiation having a wavelength greater than 200 nm.;

(d) controlling the intensity and duration of both types of irradiation of the air in the subspaces to bring the level of ozone in the selected space to an acceptable value;

(e) irradiating the stream of air with the ultraviolet radiation having a wavelength less than about 200 nm. for a chosen time interval and simultaneously selectively limiting irradiation of the stream of air with ultraviolet radiation having a wavelength greater than 200 nm. during that time interval to bring the level of ozone in the selected space to a value high enough to be dangerous to humans;

(f) at the end of the chosen time interval, reducing the irradiation of the stream of the air with the ultraviolet radiation having a wavelength less than about 200 nm. and increasing the irradiation of the stream of air with the ultraviolet radiation having a wavelength greater than 200 nm. for a second time interval sufficient to reduce the level of ozone in the selected space; and (g) permitting humans to enter the selected space after the second time interval.

* * * * *